(12) United States Patent
Kiemeneij

(10) Patent No.: US 6,723,083 B2
(45) Date of Patent: *Apr. 20, 2004

(54) CATHETER FOR PERCUTANEOUS TRANSRADIAL APPROACH

(75) Inventor: Ferdinand Kiemeneij, Bussum (NL)

(73) Assignee: Schneider (Europe) A.G. (CH)

( * ) Notice: Subject to any disclaimer, the term of this patent is extended or adjusted under 35 U.S.C. 154(b) by 0 days.

This patent is subject to a terminal disclaimer.

(21) Appl. No.: 10/246,270

(22) Filed: Sep. 18, 2002

(65) Prior Publication Data

US 2003/0018319 A1 Jan. 23, 2003

Related U.S. Application Data

(63) Continuation of application No. 09/901,401, filed on Jul. 9, 2001, now Pat. No. 6,620,150, which is a continuation of application No. 09/356,830, filed on Jul. 19, 1999, now Pat. No. 6,273,881, which is a continuation of application No. 08/899,083, filed on Jul. 23, 1997, now abandoned, which is a continuation of application No. 08/560,251, filed on Nov. 21, 1995, now abandoned.

(51) Int. Cl.[7] .................................... A61M 25/00
(52) U.S. Cl. ........................................ 604/532
(58) Field of Search .................. 604/93, 264, 525, 604/527, 532; 600/433, 434, 435

(56) References Cited

U.S. PATENT DOCUMENTS

| | | | |
|---|---|---|---|
| 4,417,886 A | 11/1983 | Frankhouser et al. | 604/53 |
| 4,735,620 A | 4/1988 | Ruiz | 604/281 |
| 4,973,306 A | 11/1990 | Ruiz | 604/53 |
| 5,188,619 A | 2/1993 | Myers | 604/280 |
| 5,203,776 A | 4/1993 | Durfee | 604/264 |
| 5,299,574 A | 4/1994 | Bower | 128/658 |
| 5,322,509 A | 6/1994 | Rickerd | 604/53 |
| 5,401,258 A | 3/1995 | Voda | 604/281 |
| 5,445,624 A | 8/1995 | Jimenez | 604/280 |
| 5,445,625 A | 8/1995 | Voda | 604/281 |
| 5,470,322 A | 11/1995 | Horzewski et al. | 604/280 |
| 5,471,986 A | 12/1995 | Ishimura et al. | 128/658 |
| 5,492,530 A | 2/1996 | Fischell et al. | 604/49 |
| 5,527,274 A | 6/1996 | Zakko | 604/280 |
| 5,531,721 A | 7/1996 | Pepin et al. | 604/282 |
| 5,569,218 A | 10/1996 | Berg | 604/282 |
| 5,584,821 A | 12/1996 | Hobbs et al. | 604/280 |
| 5,658,263 A | 8/1997 | Dang et al. | 604/280 |
| 5,725,513 A | 3/1998 | Ju et al. | 604/280 |
| 5,876,385 A | 3/1999 | Ikari et al. | 604/280 |
| 5,885,247 A | 3/1999 | Slagboom | 604/95 |
| 5,916,209 A | 6/1999 | Mick | 604/523 |
| 6,355,026 B1 * | 3/2002 | Mick | 604/523 |

FOREIGN PATENT DOCUMENTS

| | | |
|---|---|---|
| DE | G 92 15 779.3 | 3/1993 |
| EP | 0 728 494 A1 | 8/1996 |

* cited by examiner

*Primary Examiner*—Sharon Kennedy
(74) *Attorney, Agent, or Firm*—Crompton, Seager & Tufte LLC

(57) ABSTRACT

A preshaped tubular catheter for percutaneous transradial approach to catheterization, comprises a distal bridge shaped portion having a distal arch defining a primary curve, a top defining a secondary curve, and a proximal arch defining a tertiary curve. The proximal arch is connected to a straight shaft. The shaft is stiff and the bridge shaped portion has a flexibility extending at least up to and including the primary curve and a stiffness extending at least up to and including the tertiary curve.

33 Claims, 5 Drawing Sheets

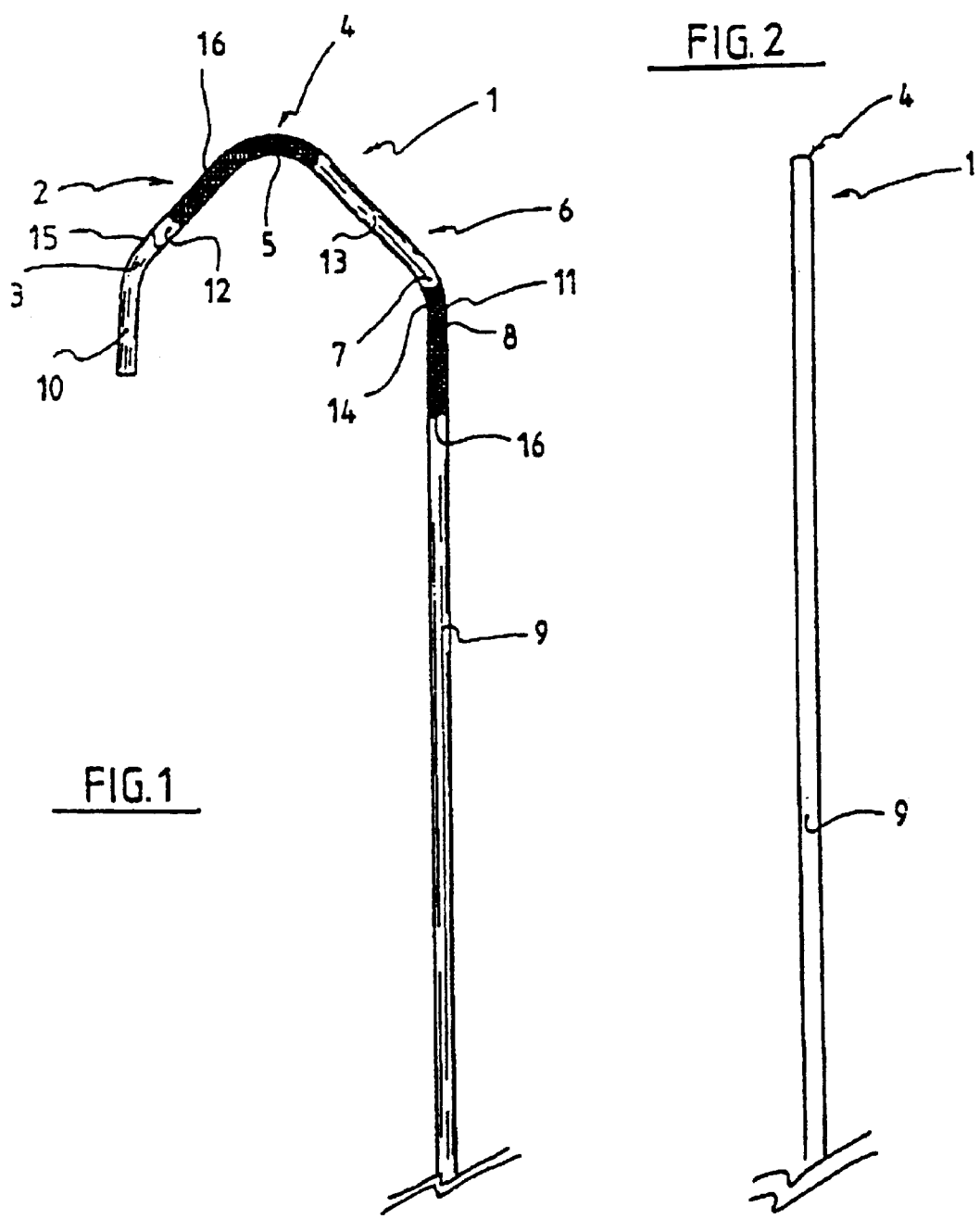

CATHETER FOR PERCUTANEOUS TRANSRADIAL APPROACH

This is a continuation of U.S. Pat. No. 6,620,150, issued Sep. 16, 2003, which in turn is a continuation of U.S. Pat. No. 6,273,881, issued Aug. 14, 2001, which in turn is a continuation of application Ser. No. 08/899,083 filed Jul. 23, 1997, now abandoned which in turn is a continuation of application Ser. No. 08/560,251 filed Nov. 21, 1995 now abandoned.

BACKGROUND OF THE INVENTION

This invention relates to preshaped tubular catheters for percutaneous transradial approach to catheterization.

Preshaped catheters are commonly used for medical procedures such as diagnosis or such as coronary angioplasty or coronary stent implantation in which they serve to guide other catheters such as pressure measuring or balloon or stent loaded balloon catheters. In these procedures, a femoral approach is currently used in which the preshaped catheter is introduced into the aorta via the femoral artery, and the catheter is then manipulated at its proximal end, by push or pull and/or torque motions, for steering its distal end into the lumen of the selected vessel. To assist in advancing the catheter through the cardiovascular system, a relatively stiff guidewire is inserted into the catheter to straighten it out and bring the tip of the catheter in the direction of origin of the selected artery prior to actual cannulation. After the catheter is inserted into the artery, the guidewire is withdrawn, and the catheter may serve for a diagnosis procedure or for the guidance of another catheter such as a balloon catheter or a stent loaded balloon catheter.

In order to properly achieve its guiding function, the preshaped catheter should have an efficient backup or stability in the region where it is placed in order to withstand the efforts and motions of the pulsating environment as well as the stresses and deformations caused by the passage of the balloon catheter or other catheter or other equipment which it guides. It should also assure a good coaxiality for proper alignment with the ostium of the artery to avoid loss of push force on the guided catheter or the risk of trauma caused by a stent loaded balloon catheter entering the vessel in a misaligned condition. Furthermore, the preshaped guiding catheter should have some automatic configurational adaptability to easily find its way through the vascular system with a minimal amount of manipulations to whenever possible reduce the load of positioning travels for the patient. It should also have an appreciable capacity to deal with a variety of take-offs or angular positions which the left coronary artery, the right coronary artery or venous by-pass grafts may have with respect to the aortic arch. And when in the selected position, the catheter should lock in place and be releasable only under longitudinal tension from the operator.

Accordingly, the preshaped guiding catheters should have a configuration of lines, curves and/or angles which precisely match the environmental context in which they will have to be used and it is therefore practically impossible to simply foresee the effects of changes made to the catheter shape.

A great number of preshaped catheters have been designed over the years for the transfemoral catheterization.

For instance, the most commonly used catheter for left coronary arteries, namely the catheter referred to as the "left Judkins" which comprises an elongated straight shaft portion followed by a distal end portion consisting of a straight portion extending from the shaft portion and followed by a curved portion for approximately 180° followed by a straight portion forming a small angle with the straight portion extending from the shaft portion, this last straight portion terminating in a tip portion substantially perpendicular thereto. This catheter is often made of a plastic material, and most of the catheters of that kind have a flexibility which is unmodulated along their length. They are also supplied in canted configurations to meet particular take-off requirements. This kind of catheter cannot be applied to right coronary arteries and, therefore, another catheter has been designed for right coronary arteries, namely the catheter referred to as the "right Judkins", also made of a plastic material, which comprises an elongated shaft portion having the shape of an elongated S terminating in a tip portion substantially perpendicular to the distal end of the S shaped shaft portion. Most of the catheters of that kind also have a flexibility which is unmodulated along their length.

Other preshaped catheters made of a plastic material, most of which have a flexibility which is unmodulated along their length have been designed, for example the catheters described in the document WO 92/12 754 the purpose of which is to improve over the "Judkins" catheters. According to a first embodiment, intended for left coronary arteries, the catheter comprises a first straight shaft portion followed by a distal end portion comprising a second straight portion extending at an angle to the first straight portion, followed by a curved portion for approximately 180° followed by a third straight portion substantially parallel to the second straight portion, and a tip portion extending from and at an angle from the third straight portion, this tip portion extending behind the first straight shaft portion; this catheter is adapted for use with a relatively stiff wire inserted therein. A second embodiment, also intended for left coronary arteries and for use with a stiff wire inserted therein comprises an elongated first straight shaft portion followed by a distal end portion consisting of a second straight portion extending at an angle to the first straight shaft portion, a curved portion extending from the second straight portion for approximately 180°, a third straight portion extending from the curved portion at an angle to the second straight portion, and a tip portion extending at an angle to the third straight portion and parallel to the second straight portion, the tip portion extending behind the first straight portion. A third embodiment, also intended for left coronary arteries and use with a stiff guiding wire, and more particularly for left coronary arteries which are angularly displaced posteriorly from their normal distance (a situation referred to as posterior take-off), comprises a first straight portion extending from the proximal end of the catheter, and a distal end portion consisting of a second straight portion extending at an angle to the first straight portion and followed by a curved portion extending for approximately 180°, the curved portion being followed by a third portion terminating in a tip portion; in this catheter, the first and third straight portions are bent out of the plane formed by the second straight portion and the curved portion. A fourth embodiment intended for use with a stiff guidewire in a right coronary artery that is angularly displaced from its normal position and has an anterior take-off, comprises a first straight portion and a distal end portion formed by a second straight portion extending from the first straight portion at an angle in a first plane which is between 50° and 70° and at an angle in a second plane which is perpendicular to the first plane which is between 20° and 40°; a third straight tip portion extends from the second straight portion at an angle which is between 20° and 30° in the first plane and at an angle between 40° and 50° to the second straight portion. A fifth embodiment, intended for use with a stiff guidewire in a venous by-pass connecting the aorta to the distal segment of the right coronary artery, comprises a first straight shaft portion and a distal end portion consisting of a first curved portion extending the first straight portion, a second curved portion extending the first curved portion oppositely thereto and followed by a straight tip portion parallel to the first straight portion.

Still other preshaped catheters are available on the market such as, for instance, the catheter referred to as the "left Amplatz" or the "right Amplatz" which is constructed on variations of a basic shape having a straight elongated shaft followed by a first curve in a first direction followed by a second curve in the opposite direction, or the catheter referred to as the "Multipurpose" which bases on a shape having a substantially straight shaft portion followed by a curve, most of which have a flexibility which is unmodulated along their length.

A percutaneous transradial approach to catheterization is now being investigated because of favorable anatomical relations of the radial artery to its surrounding structures and the double blood supply to the hand. Potential benefits of this approach are safe transarterial coronary interventions combining rapid mobilization of the patient after intervention, with the resulting reduced hospitalization, and easy, safe, and effective hemostasis leading to a marked reduced incidence of access-site related major complications.

So far, there are, however, no specific catheters available for this technique. Typically, catheters such as those referred to hereinabove, which are specific to percutaneous transfemoral catheterization approach, have been used, however with relative lack of success on backup and coaxiality in alignment with the artery. Furthermore, they usually require a straightening wire for bringing the tip of the catheter in the direction of the ostium of the artery. And a plurality of catheters is needed to meet the various take-off configurations; and even so, they need some tricks to be properly used.

It is therefore an object of the present invention to improve the percutaneous transradial approach to catheterization by proposing a catheter specific to transradial catheterization. It is a further object of the invention to provide a catheter for transradial approach which avoids the drawbacks of the catheters for femoral approach used for transradial approach. Still a further object of the invention is to provide a catheter for transradial approach which is simple to manufacture with available techniques, and which avoids unnecessary costs as well as complex stock supply or ordering procedures.

SUMMARY OF THE INVENTION

Accordingly, the combination of a flexible primary curve with stiff structures provides modulated flexibility and allows selective cannulation of right coronary arteries, left coronary arteries, and venous by-pass grafts. It also permits dealing with a variety of take-off conditions of the right coronary artery, the left coronary artery and venous by-pass grafts. As it permits to bring the tip of the catheter in the direction of the origin of the coronary artery, prior to any cannulation, there is an improved coaxiality of the catheter. Deep intubation across sharp curves of coronary irregularities is also possible. The stiff structures assure support on contralateral aortic sinus and extra support against aortic wall; they optimize the torque and kink resistance during catheter manipulations; they also optimize the support for easier manipulation and change of angles of the primary curve; and once the catheter is positioned they assure full backup to the catheter.

As a result, there is no need for a guidewire to bring the tip of the catheter in the direction of the origin of the coronary, prior to cannulation. There is a smooth passage of stents by reduced friction at the site of the catheter curves. The success of stent delivery is thus greatly improved and stent implantation may become a current procedure, not only for elective cases, and without the need to exchange guiding catheters.

A further advantage is that the catheter has a multipurpose capacity for dealing with right coronary arteries, left coronary arteries, and venous by-pass grafts, without the necessity to exchange catheters during a multivessel procedure, thereby preventing artery spasm and discomfort, potential loss of distal access in case of extreme tortuosity, long procedural and fluoro time, as well as unnecessary costs and heavy stock procedures.

And of course the catheter has compatibility for percutaneous transluminal coronary angioplasty, perfusion, stent delivery and diagnostic.

In sum, the present invention relates to a preshaped tubular catheter for percutaneous transradial approach to catheterization, having a distal bridge shaped portion having a distal arch defining a primary curve, a top defining a secondary curve, and a proximal arch defining a tertiary curve. The proximal arch is connected to a distal end of a straight and stiff shaft, and the bridge shaped portion has a flexibility extending at least up to and including the primary curve and a stiffness extending at least up to and including the tertiary curve. The distal bridge shaped portion may have a first distal straight portion, a primary curve extending from the first distal straight portion, the primary curve having a concavity oriented towards a proximal end of the bridge shaped portion, a second straight portion extending from the primary curve, the second straight portion being inclined towards the proximal end of the bridge shaped portion, a secondary curve extending from the second straight portion, the secondary curve having a concavity oriented between the first distal straight portion and the proximal end of the bridge shaped portion, a third straight portion extending from the secondary curve, the third straight portion being inclined towards the proximal end of the bridge shaped portion, and a tertiary curve extending from the third straight portion, the tertiary curve having a concavity oriented towards the first distal straight portion, and the tertiary curve having a proximal end connected to the distal end of the straight shaft. The flexibility of the bridge shaped portion may extend at least over the first distal straight portion, the primary curve, and a distal portion of the second straight portion. The secondary curve may extend over about 90°, and the tertiary curve may extend over about 45°. The second straight portion and the third straight portion may be essentially the same length. The first distal straight portion may be substantially parallel to the straight shaft.

The above and other objects, features and advantages of the invention will become readily apparent from the following detailed description with reference to the accompanying drawings which show, diagrammatically and by way-of example only, a preferred but still illustrative embodiment of the invention.

DESCRIPTION OF THE DRAWINGS

FIGS. 1 and 2 are side and front views, respectively of a portion of the catheter according to the invention.

DESCRIPTION OF PREFERRED EMBODIMENTS

Figure 3:
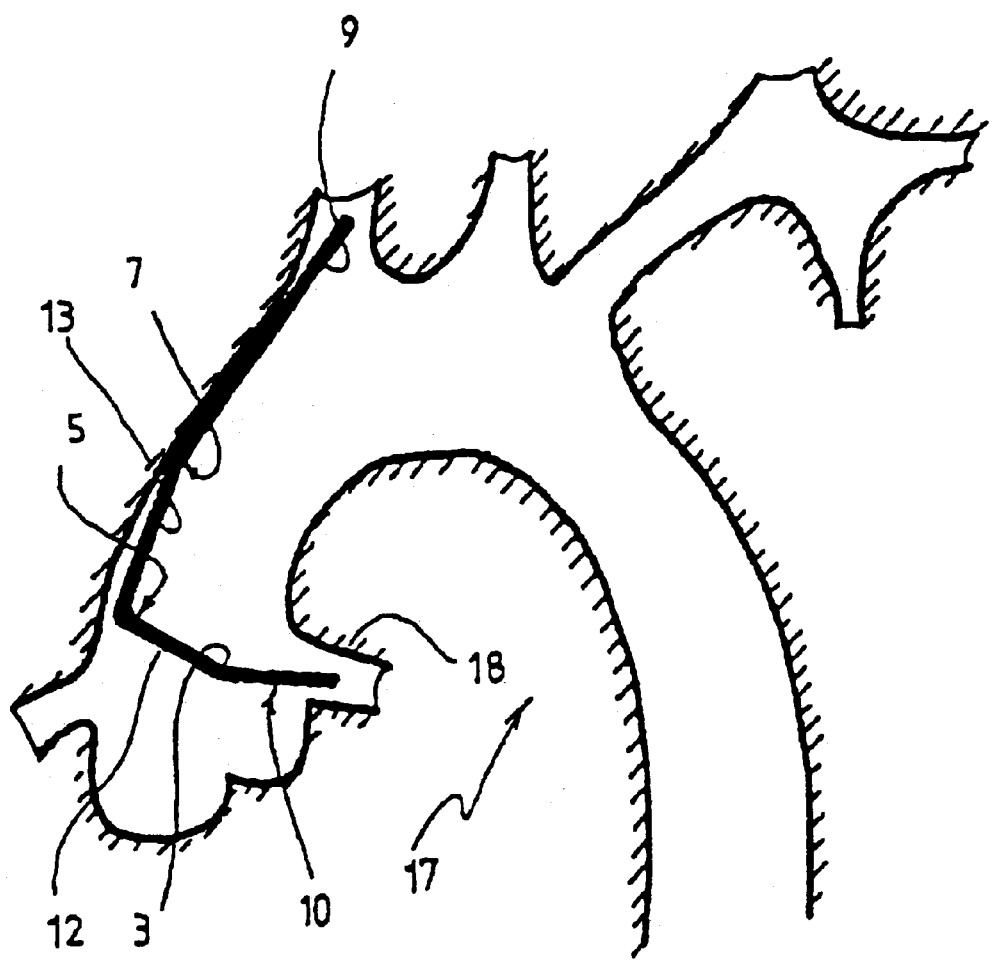
FIGS. 3, 4 and 5 are, respectively, cross sectional views of a portion of a cardiovascular system with the catheter inserted in the left coronary artery.

The catheter shown in FIGS. 1 and 2 is tubular and comprises a distal bridge shaped portion 1 having a distal arch 2 defining a primary curve 3, a top 4 defining a secondary curve 5, and a proximal arch 6 defining a tertiary curve 7. The proximal arch 6 is connected to a distal end 8 of a straight shaft 9 the proximal end of which is fitted with the usual handling connector (not shown). The shaft 9 is stiff and the bridge shaped portion 1 has a flexibility extending at least up to and including the primary curve 3 and a stiffness extending at least up to and including the tertiary curve 7.

More specifically, the bridge shaped portion 1 comprises a first distal straight portion 10, a first primary curve 3 extending from said first straight portion 10, which primary curve has a concavity oriented towards the proximal end 11 of the bridge shaped portion 1. A second straight portion 12 extends from primary curve 3 and is inclined towards the proximal end 11 of the bridge shaped portion 1. A secondary curve 5 extends from the second straight portion 12 and said secondary curve has a concavity oriented between the first distal straight portion 10 and the proximal end 11 of bridge shaped portion 1. A third straight portion 13 extends from the secondary curve 5, and said straight portion 13 is inclined towards the proximal end 11 of bridge shaped portion 1. A tertiary curve 7 extends from third straight portion 13, and said tertiary curve has a concavity oriented towards the first distal straight portion 10; a proximal end 14 of said tertiary curve is connected to the distal end 8 of the shaft 9.

The shaft 9 is stiff and, preferably, the flexibility of the bridge shaped portion 1 extends over the first distal straight portion 10, the primary curve 3 and a distal portion 15 of second straight portion 12 while the proximal part of second straight portion 12, the secondary curve 5, the third straight portion 13 and the tertiary curve 7 are stiff. Stiffness may be obtained, for example, by a braiding 16 embedded in the plastic material forming the catheter or otherwise, for example, by quality of the material at the appropriate regions.

Preferably, the secondary curve extends over about 90° and the tertiary curve extends over about 45°. However, these data may be selected otherwise.

In a preferred embodiment, the second straight portion 12 and the third straight portion 13 are essentially of the same length. Another choice is however possible, for instance the second and third straight portions may have a differing length.

The first distal straight portion 10 may be, as shown, substantially parallel to the straight shaft 9. However, this first distal straight portion 10 may be selected at an angle opening in the direction of straight shaft 9.

Instead of extending up to the distal portion 15 of second straight portion 12, the flexibility of the bridge shaped portion 1 may extend closer to the primary curve 3 or proximally beyond the distal portion 15 of second straight portion 12.

The distal end of first distal straight portion 10 may be fitted with a soft tip to be fully atraumatic.

FIGS. 3 through 6 illustrate a catheter entering a patient's aorta through the brachiocephelic artery. The brachiocephelic artery can be reached by accessing the patient's vasculature through the patient's arm.

FIG. 3 shows a cardiovascular system 17 in which the left coronary artery 18 has a horizontal take-off. As may be seen, the tertiary curve 7 rests on the aortic wall; upon pulling the catheter, the secondary curve 5 will deflect the primary curve 3 so that the first straight portion 10 coaxially engages the ostium of the artery.

Figure 4:
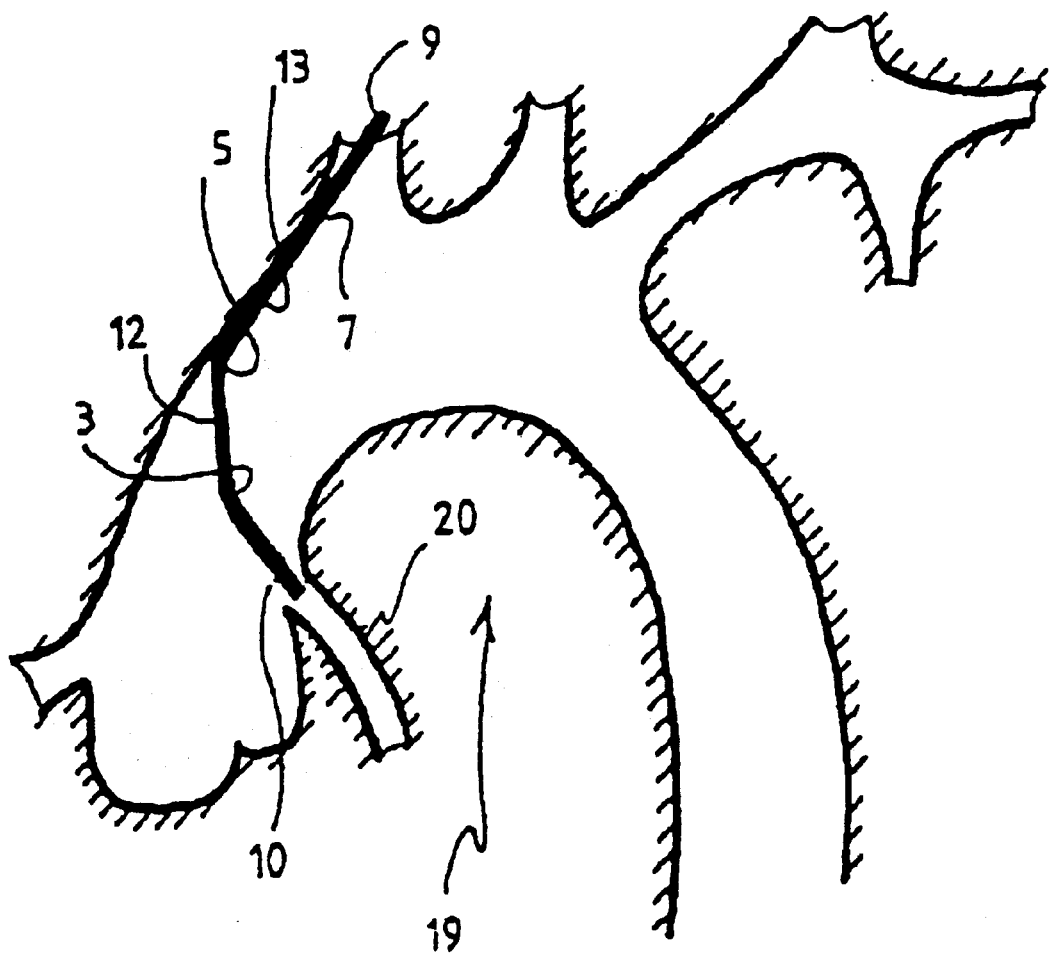

FIG. 4 shows a cardiovascular system 19 in which the left coronary artery 20 has a downward take-off. In this situation a pull on the catheter will modify the support conditions of secondary and tertiary curves 5 and 7 to redirect primary curve 3 and first straight portion 10 in the direction of the ostium of the artery.

Figure 5:
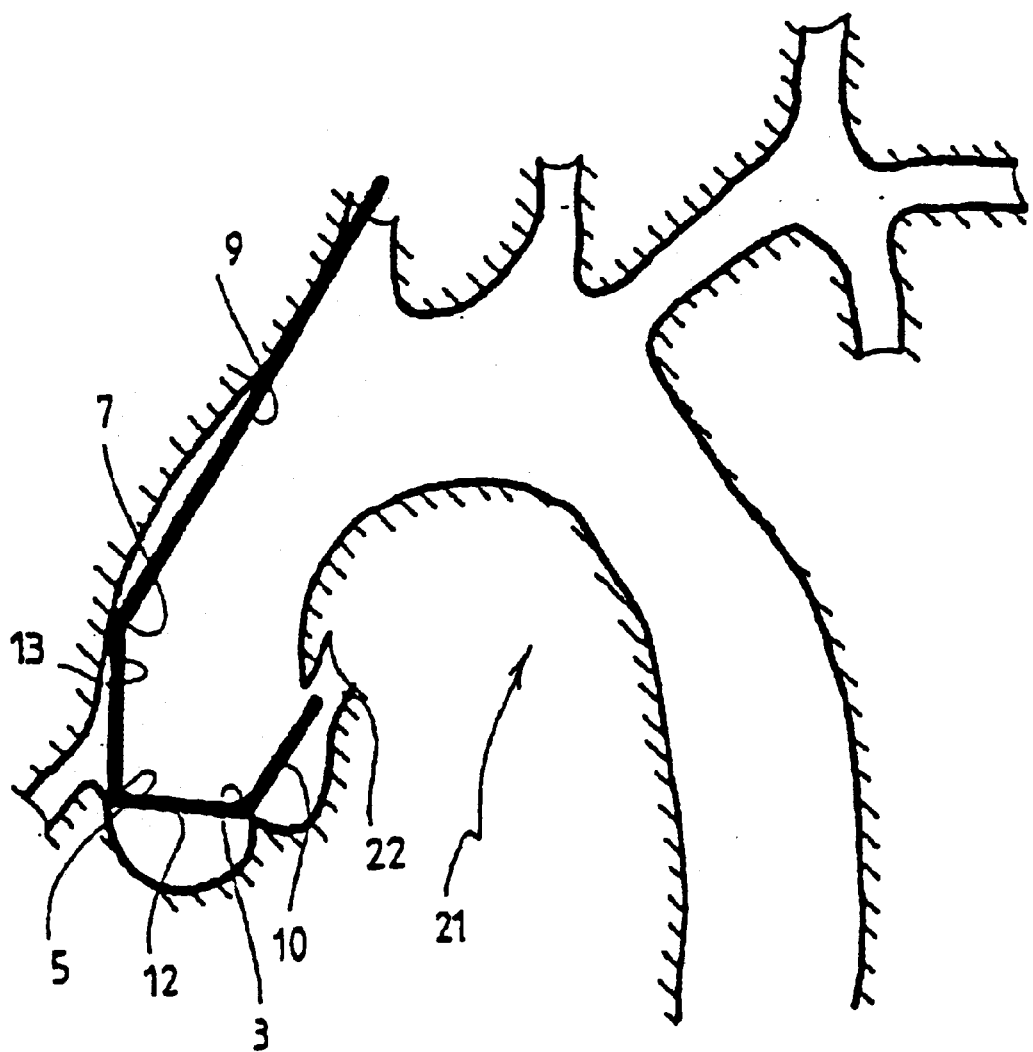

FIG. 5 shows a cardiovascular system 21 in which the left coronary artery has a vertical take-off. In such a condition, the catheter will need a push so that the tertiary curve 7 lies deeper in the root whereby the secondary curve 5 will divert the primary curve 3 to have it take a more vertical position to secure coaxiality of the first straight portion 10 with the ostium of the artery.

Figure 6:
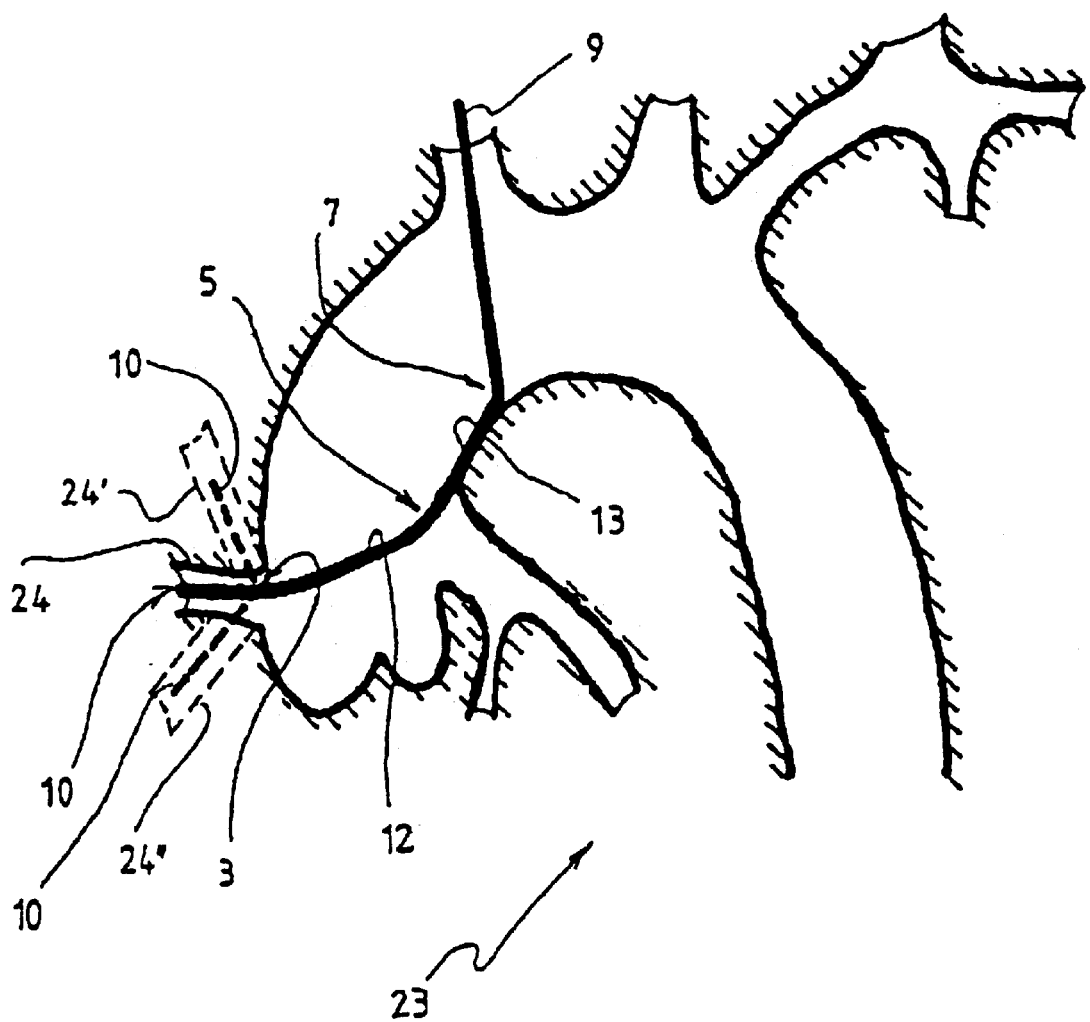
FIG. 6 is a cross sectional view of a portion of a cardiovascular system with the catheter inserted in the right coronary artery.

FIG. 6 shows a cardiovascular system 23 in which the right coronary artery is shown in a horizontal take-off 24, respectively in upward take-off 24', respectively in a downward take-off 24". As may be seen, the tertiary curve 7 and secondary curve 5 assure a correct directioning of primary curve 3 and first straight portion 10 in coaxial alignment with the artery. To achieve engagement into the upward take-off 24', a push on the shaft 9 of the catheter will give an upward deflection of primary curve 3 and the corresponding upward directioning of first straight portion 10 to coaxially engage the artery. Engagement into the downward take-off 24" will require a pull on shaft 9 of the catheter so that the primary curve 3 will take a more downward deflection which will re-direct downwardly the first straight portion 10 to properly engage the ostium coaxially.

As may be seen, in all these conditions, the catheter has a strong back-up due to the supporting condition of the tertiary curve, and/or secondary curve, and/or third straight portion.

What is claimed is:

1. A preshaped tubular catheter for percutaneous transradial approach to catheterization, comprising:

a distal bridge portion having a distal portion defining a primary curve, a top defining a secondary curve, and a proximal portion defining a tertiary curve, wherein said proximal portion is connected to a distal end of a generally straight shaft, and wherein said bridge portion has a more flexible portion extending at least up to the primary curve and a portion less flexible than the flexible portion extending at least up to said tertiary curve;

means for advancing the bridge portion through either a radial artery or a femoral artery to a region adjacent a coronary artery of a patient;

wherein the bridge portion includes a generally straight distal region disposed distal to the primary curve; and means for co-axially aligning the distal region within the coronary artery when the catheter is advanced through either the radial artery or the femoral artery.

2. A catheter, comprising:

a distal bridge portion including a first straight region, a second straight region, a third straight region, a fourth straight region, a primary curve disposed between the first and second straight regions, a secondary curve disposed between the second and third straight regions, a tertiary curve disposed between the third and fourth straight regions;

a proximal shaft portion connected to the fourth straight region;

wherein the bridge portion has a more flexible portion extending at least up to the primary curve and a portion less flexible than the flexible portion extending at least up to the tertiary curve;

means for advancing the bridge portion through either a radial artery or a femoral artery to a region adjacent a coronary artery of a patient; and means for co-axially aligning the first straight region within the coronary artery when the catheter is advanced through either the radial artery or the femoral artery.

3. A method of positioning a catheter, comprising steps of:

providing a catheter including an elongate shaft having a distal straight portion, a proximal straight portion, and a curved portion disposed between the distal and proximal straight portions, the curved portion including a primary curve disposed adjacent to the distal straight portion, a tertiary curve disposed adjacent to the proximal straight portion, and a secondary curve disposed between the primary and tertiary curves;

advancing the catheter through a blood vessel within an arm of a patient until the curved portion of the catheter is disposed within an aorta of the patient;

positioning the curved portion so that the tertiary curve rests against a wall of the aorta opposite an ostium of the coronary artery;

applying a force to the proximal straight portion; and deflecting the curved portion so that the distal straight portion of the catheter is co-axially aligned with the coronary artery.

4. The method of claim 3, wherein the step of positioning the curved portion includes positioning the tertiary curve against a wall of the aorta opposite an ostium of a horizontally directed left coronary artery.

5. The method of claim 4, wherein the step of deflecting the curved portion includes co-axially aligning the distal straight portion with the horizontally directed left coronary artery.

6. The method of claim 3, wherein the step of positioning the curved portion includes positioning the tertiary curve against a wall of the aorta opposite an ostium of a downwardly directed right coronary artery.

7. The method of claim 6, wherein the step of deflecting the curved portion includes co-axially aligning the distal straight portion with the downwardly directed right coronary artery.

8. The method of claim 3, wherein the step of positioning the curved portion includes positioning the tertiary curve against a wall of the aorta opposite an ostium of a downwardly directed left coronary artery.

9. The method of claim 8, wherein the step of deflecting the curved portion includes co-axially aligning the distal straight portion with the downwardly directed left coronary artery.

10. The method of claim 3, wherein the step of advancing the catheter through a blood vessel within an arm of a patient includes advancing the catheter through a radial artery.

11. The method of claim 3, wherein the step of advancing the catheter through a blood vessel within an arm of a patient includes advancing the catheter through a brachiocephalic artery.

12. The method of claim 3, wherein the step of applying a force to the proximal straight portion includes applying a pulling force to the proximal straight portion.

13. The method of claim 3, wherein the step of applying a force to the proximal straight portion includes applying a pushing force to the proximal straight portion.

14. A method of positioning a catheter, comprising steps of:

providing a catheter including a tubular shaft having a distal straight portion, a proximal straight portion, and a curved portion disposed between the distal and proximal straight portions, the curved portion including a primary curve disposed adjacent to the distal straight portion, a tertiary curve disposed adjacent to the proximal straight portion, and a secondary curve disposed between the primary and tertiary curves;

advancing the catheter through an artery located within an arm of a patient until the curved portion of the catheter is disposed adjacent an aorta of the patient;

positioning the curved portion of the tubular shaft so that the tertiary curve rests against a wall of the aorta opposite an ostium of the coronary artery; and deflecting the curved portion so that the distal straight portion of the catheter is co-axially aligned with the coronary artery.

15. The method of claim 14, wherein the step of positioning the curved portion includes positioning the tertiary curve against a wall of the aorta opposite an ostium of a horizontally directed left coronary artery.

16. The method of claim 15, wherein the step of deflecting the curved portion includes co-axially aligning the distal straight portion with the horizontally directed left coronary artery.

17. The method of claim 14, wherein the step of positioning the curved portion includes positioning the tertiary curve against a wall of the aorta opposite an ostium of a downwardly directed right coronary artery.

18. The method of claim 17, wherein the step of deflecting the curved portion includes co-axially aligning the distal straight portion with the downwardly directed right coronary artery.

19. The method of claim 14, wherein the step of positioning the curved portion includes positioning the tertiary curve against a wall of the aorta opposite an ostium of a downwardly directed left coronary artery.

20. The method of claim 19, wherein the step of deflecting the curved portion includes co-axially aligning the distal straight portion with the downwardly directed left coronary artery.

21. The method of claim 14, wherein the step of advancing the catheter through an artery within an arm of a patient includes advancing the catheter through a radial artery.

22. The method of claim 14, wherein the step of advancing the catheter through an artery within an arm of a patient includes advancing the catheter through a brachiocephalic artery.

23. The method of claim 14, wherein the step of deflecting the curved portion so that the distal straight portion of the catheter is co-axially aligned with the coronary artery includes applying a pulling force to proximal straight portion.

24. The method of claim 14, wherein the step of deflecting the curved portion so that the distal straight portion of the catheter is co-axially aligned with the coronary artery includes applying a pushing force to proximal straight portion.

25. A method of positioning a catheter adjacent the coronary artery of a patient, comprising the steps of:

providing a percutaneous transradial catheter, the catheter including a generally tubular shaft having a distal straight region, a proximal straight region, and a curved region disposed between the distal and proximal straight regions, the curved portion including a tertiary curve disposed adjacent the proximal straight region, a primary curve disposed adjacent the distal straight region, and a secondary curve disposed between the tertiary curve and the primary curve;

surgically creating an incision within an arm of a patient;

identifying a blood vessel adjacent the incision;

advancing the catheter through the blood vessel to a position adjacent an aorta of the patient;

positioning the curved region so that the tertiary curve rests against a wall of the aorta opposite an ostium of a coronary artery;

applying a force to the proximal straight region; and deflecting the curved region so that the distal straight region of the region is co-axially aligned with the coronary artery.

26. The method of claim 25, wherein the step of positioning the curved region includes positioning the tertiary curve against a wall of the aorta opposite an ostium of a horizontally directed left coronary artery.

27. The method of claim 26, wherein the step of deflecting the curved region includes co-axially aligning the distal straight region with the horizontally directed left coronary artery.

28. The method of claim 25, wherein the step of positioning the curved region includes positioning the tertiary curve against a wall of the aorta opposite an ostium of a downwardly directed right coronary artery.

29. The method of claim 28, wherein the step of deflecting the curved region includes co-axially aligning the distal straight region with the downwardly directed right coronary artery.

30. The method of claim 25, wherein the step of positioning the curved region includes positioning the tertiary curve against a wall of the aorta opposite an ostium of a downwardly directed left coronary artery.

31. The method of claim 30, wherein the step of deflecting the curved region includes co-axially aligning the distal straight region with the downwardly directed left coronary artery.

32. The method of claim 25, wherein the step of applying a force to the proximal straight region includes applying a pulling force to proximal straight region.

33. The method of claim 25, wherein the step of applying a force to the proximal straight region includes applying a pushing force to proximal straight region.

* * * * *